(12) United States Patent
Poelstra et al.

(10) Patent No.: US 7,348,313 B2
(45) Date of Patent: Mar. 25, 2008

(54) METHOD FOR TARGETING CELLS INVOLVED IN SCLEROTIC AND/OR FIBROTIC DISEASES

(75) Inventors: Klaus Poelstra, Buitenpost (NL); Eleonora Beljaars, Groningen (NL); Drik Klaus Fokke Meijer, Groningen (NL); Detlef Bruno Igor Schuppan, Bubenreuth (DE)

(73) Assignees: Stichting Voor de Technische Wetenschappen, Utrecht (NL); Rijksuniversiteit Groningen, Groningen (NL)

( * ) Notice: Subject to any disclaimer, the term of this patent is extended or adjusted under 35 U.S.C. 154(b) by 0 days.

(21) Appl. No.: 11/012,056

(22) Filed: Dec. 15, 2004

(65) Prior Publication Data

US 2005/0227916 A1     Oct. 13, 2005

Related U.S. Application Data

(62) Division of application No. 09/806,837, filed as application No. PCT/NL98/00579 on Oct. 8, 1998, now Pat. No. 6,844,319.

(51) Int. Cl.
*A61K 31/7004* (2006.01)
(52) U.S. Cl. .......................... 514/23; 514/776
(58) Field of Classification Search ..................... None
See application file for complete search history.

(56) References Cited

FOREIGN PATENT DOCUMENTS

EP          0844252 A    5/1998
WO     WO 97/46099 A    12/1997

OTHER PUBLICATIONS

Albanis Friedman, Am. J. Transplant., 2006, 6, 12-19.*
Bataller & Brenner, J. Clin. Invest., 2005, 115, 209-18.*
Gressner & Weiskirchen, J. Cell. Mol. Med., 2006, 10, 76-99.*
Chuang et al., Pharm. Res., 2002, 19, 569-77.*
Bruck et al. Liver Int., 2004, 24, 169-76, abstract only.*
Goto, M., The Liver-Cell Specific Drug Delivery System, Nippon Rinsho (Aug. 1994), 52(8):2214-24.
Beljaars et al., The Development of novel albumin carriers to hepatic stellate by application ofcyclopeptide moieties recognizing collage type VI and platelet derived growth factor receptors, HEPATOLOGY, (Oct. 1998) vol. 28, No. 4 Part 2, PP. 313A (Abstract 602) Meeting Info: Biennial Scientific Meeting of the International Association for the Study of the Liver and the 49th Annual Meeting and Postgraduate Courses of the American Association for the . . . .
Beljaars et al., Mannose 6-phosphate modified albumin accumulates in hepatic stellate cells: Potential application as an antifibroti drug carrier, HEPATOLOGY, (Oct. 1998) vol. 28, No. 4 Part 2, pp. 233A (Abstract 282) Meeting Info: Biennial Scientific Meeting of the International Association for the Study of the Liver and the 49th Annual Meeting and Postgraduate Courses of the American Association for the . . . .
Delforge et al., Design of a synthetic adhesion protein by grafting RGD tailed cyclic peptides on bovine serum albumin, Lett. Pept. Sci. (1998) 5(2-3) 87-91 (Chem. Abs. 126:260818).

* cited by examiner

*Primary Examiner*—Cecilia J. Tsang
*Assistant Examiner*—Christina M. Bradley
(74) *Attorney, Agent, or Firm*—Kendrew H. Colton; Fitch, Even, Tabin & Flannery

(57) ABSTRACT

A compound includes a carrier molecule wherein the carrier molecule is linked to a further molecule, wherein the further molecule is at least one cyclic peptide in which the cyclic peptide portion thereof contains at least one sequence encoding a cell receptor recognizing peptide (RRP) and with the proviso that the compound is not a naturally occurring receptor agonist or antagonist. Preferably, the RRP is a receptor specific for Hepatic Stellate Cells (HSC) or a receptor that is up-regulated on HSC during disease. The RFP may be chosen from among a PDGF receptor, a collagen type VI receptor, cytokine receptor(s) such as TGB$\beta$, INF$\alpha$ and interleukin$\beta$. The cyclic portion of the peptide can contain at least one amino acid sequence RGD or KPT. The compounds can be used as an active targeting ingredient for manufacturing a pharmaceutical composition for therapy, prophylaxis or diagnosis of a disease chosen from fibrotic disease, sclerotic disease, and chronic or acute inflammatory processes including glomeruloscherosis, interstitial fibrosis, lung fibrosis, atherosclerosis, rheumatoid arthritis, Crohns disease, colitis ulcerosa, glomerulonephritis and sepsis, and particularly for targeting HSC. Pharmaceutical compositions contain the above-compound(s).

6 Claims, 6 Drawing Sheets

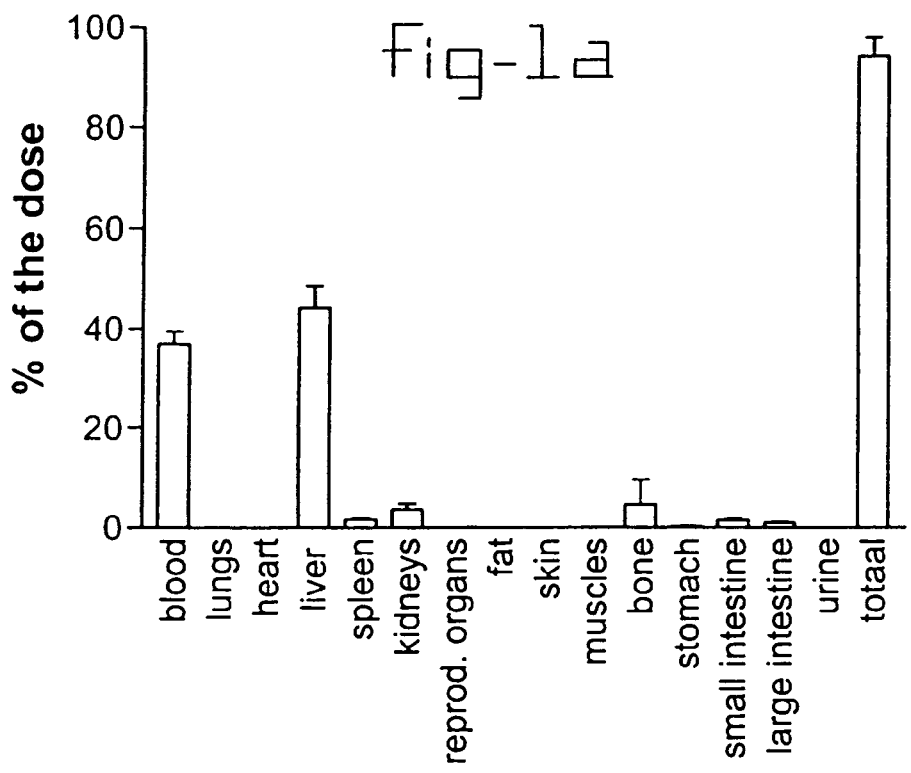
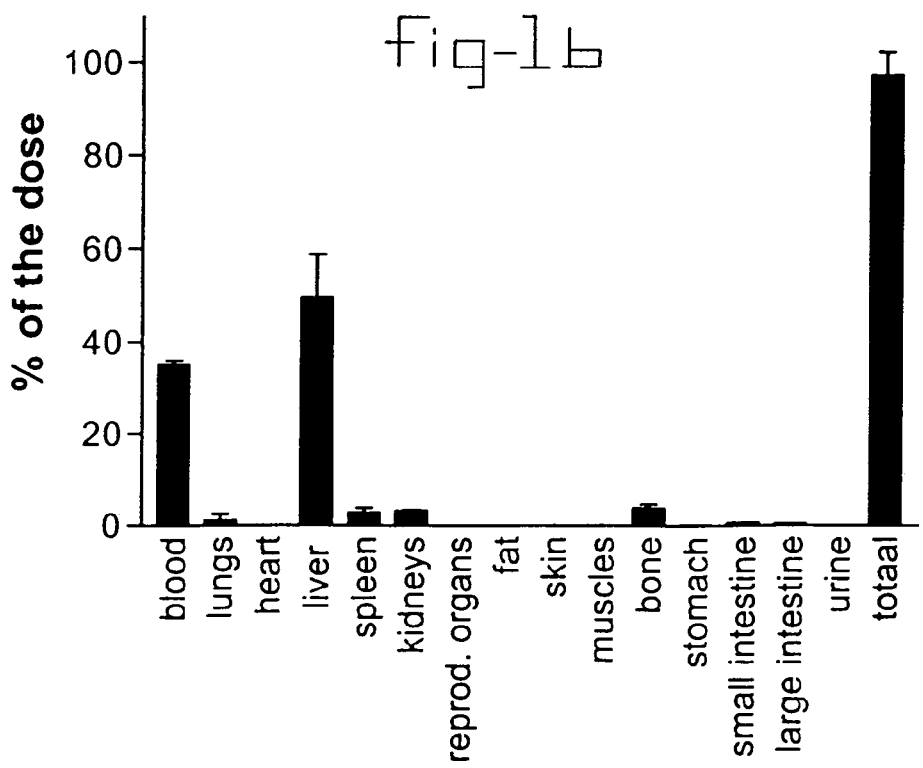

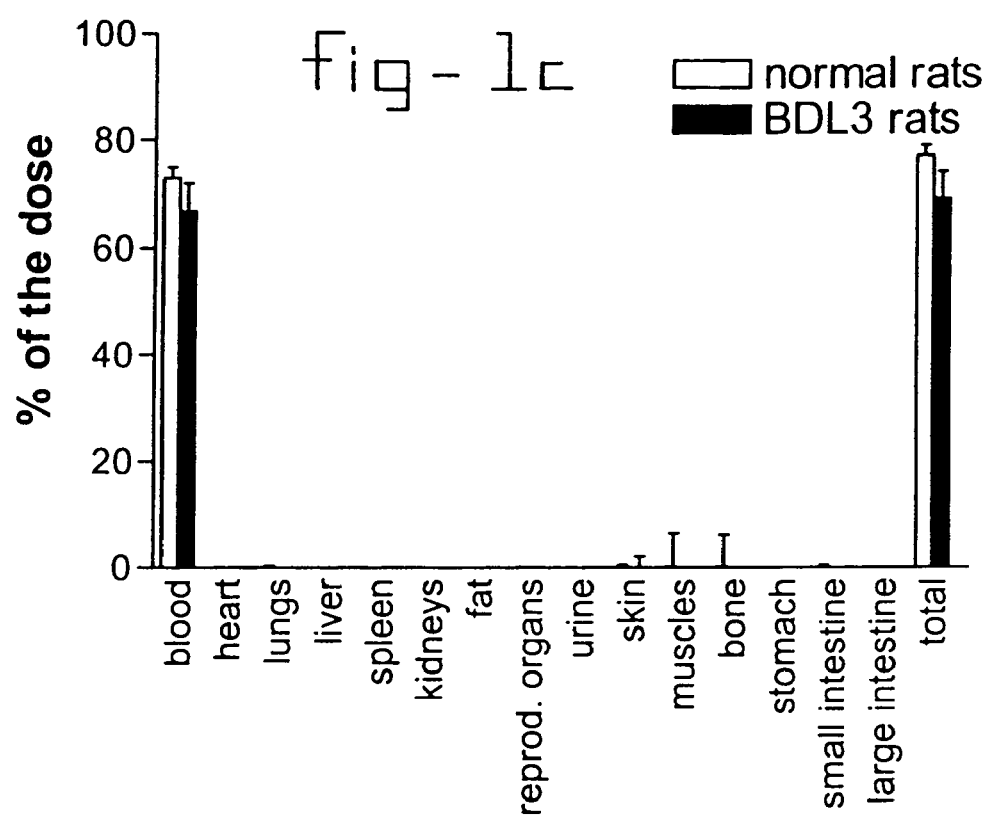

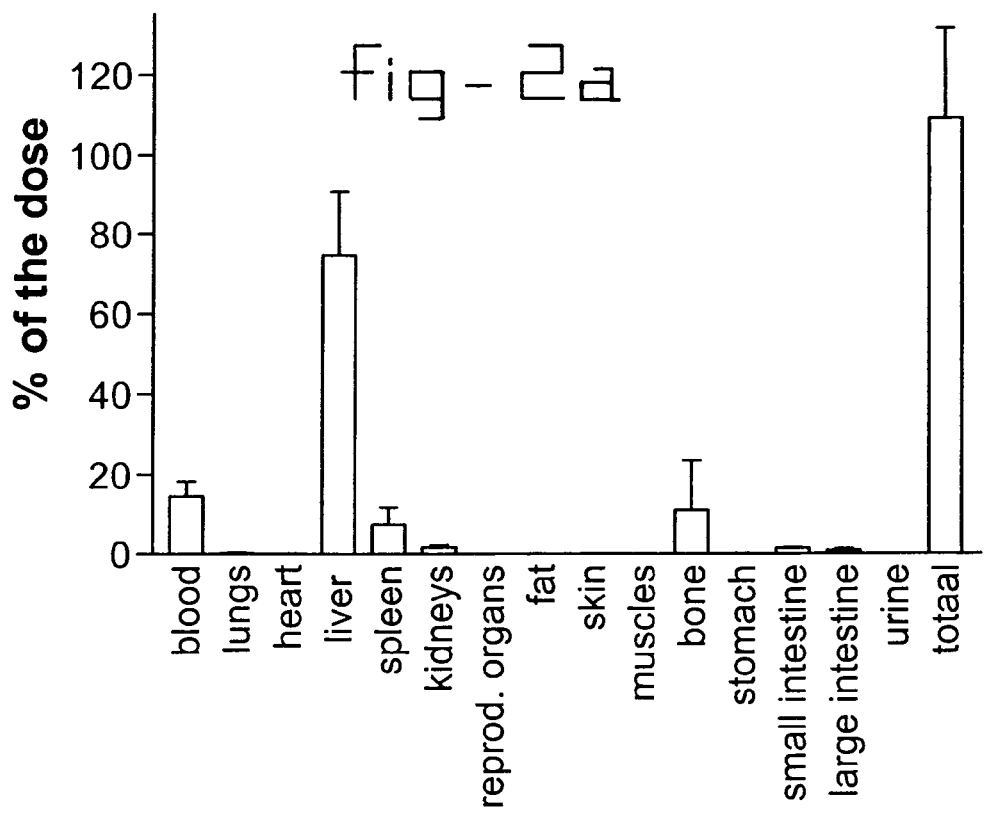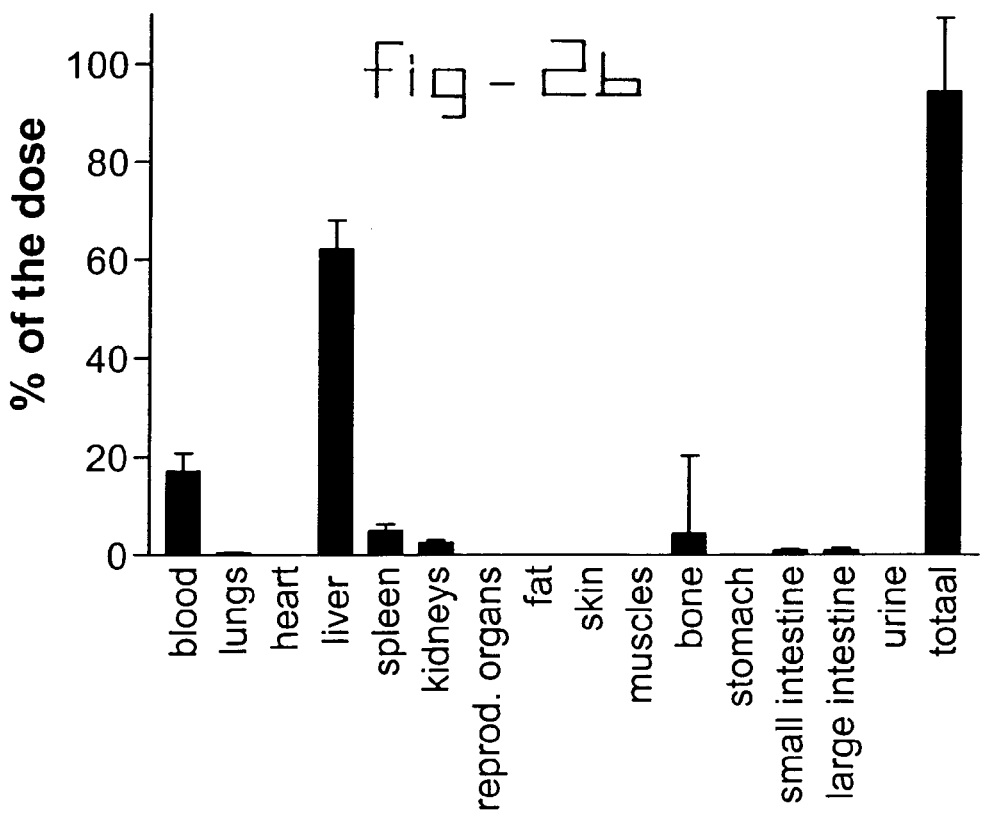

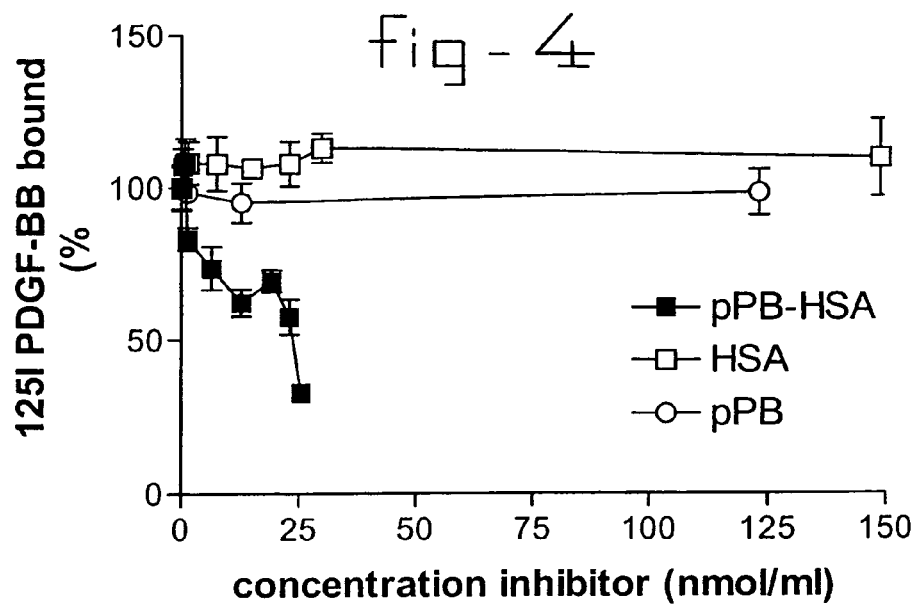
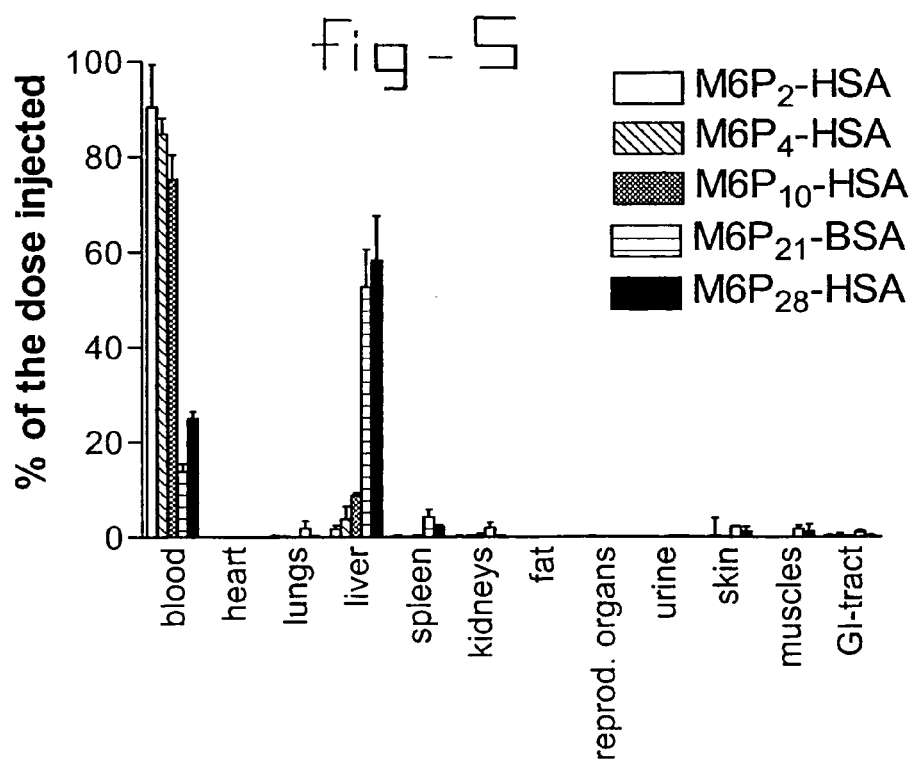

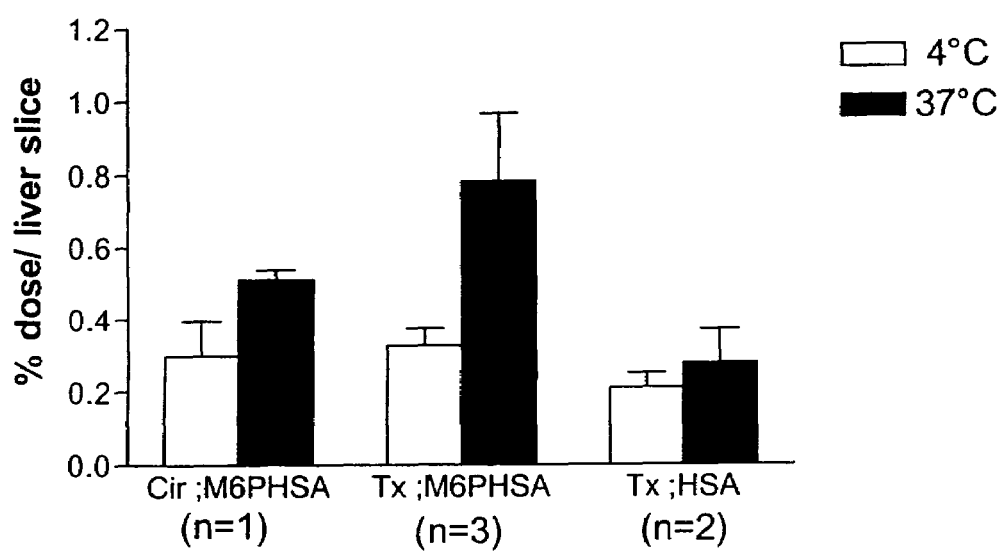

METHOD FOR TARGETING CELLS INVOLVED IN SCLEROTIC AND/OR FIBROTIC DISEASES

RELATED APPLICATIONS

This is a divisional application of U.S. application Ser. No. 09/806,837 filed Jul. 23, 2001, now U.S. Pat. No. 6,344,319 B1, the complete disclosure of which, including sequence listing(s) is incorporated herein by reference, which is the National Phase of International Application PCT/NL98/00579 filed Oct. 8, 1998, which designated the United States and that International Application was published under PCT Article 21(2) in English.

FIELD OF THE INVENTION

The inventions relate to methods for for targeting cells involved in sclerotic and/or fibrotic diseases in a tissue sample or subject and a composition adapted for used in the diclosed methods.

BACKGROUND OF THE INVENTION

The hallmark of fibrosis is the excessive deposit of extracellular matrix components caused by an increased synthesis and decreased degradation of matrix proteins, predominantly collagen type I and III. This process of fibrosis can occur in all kinds of organs such as the kidney (glomerulosclerosis or interstitial fibrosis), the skin (scar formation), the lung and also in the liver, where the end-stage of liver fibrosis is referred to as cirrhosis. The process also shares many characteristics with the formation of atherosclerotic plaques in arteries. Liver fibrosis leads to a deterioration of liver function, and eventually in complete liver failure, which is lethal if untreated. The process can be elicited by viruses (Hepatitis A, B and C), alcohol consumption, genetic disorders, or by chronic exposure to hepatotoxic agents. The incidence of this disease is very variable depending on the country. In the period 1985-1989, the incidence of liver cirrhosis in The Netherlands was 3.90 per 100,000 habitants per year, whereas this incidence in, for instance, France and Germany was 11.9 respectively 12.4. To date, no effective pharmacotherapeutic intervention is available for this disease. In the past decades liver transplantation has become a serious option for many patients but the costs, the availability of donor livers and the traumatic event of the transplantation itself hamper the application of such an operation in general practice. Pharmacological intervention would be a better option.

Hepatic stellate cells (HSC), also called Ito cells or fat storing cells strongly proliferate during the progression of the disease and they subsequently transform into myofibroblasts (MF). These cells are the major producers of collagens, glycoproteins, and proteoglycans in a diseased liver. Moreover, HSC and MF produce an array of mediators which activate other hepatic and inflammatory cells thus enhancing the fibrotic process. Therefore, HSC are an important target for anti-fibrotic therapy. However, in vivo studies indicate that anti-fibrotic drugs are not efficiently taken up by HSC and as a consequence, most drugs which showed potent anti-fibrotic activity in vitro, failed to exert any effect in vivo. At high doses such drugs often induce many side effects caused by extrahepatic distribution of the drug. Cell specific delivery is an option to solve these problems. This can be accomplished by coupling drugs to carrier molecules, which are selectively taken up by the target cells. Liposomes are well known drug carriers but modified proteins can also be applied. Cell specific delivery of therapeutic and diagnostic agents to hepatocytes, endothelial and Kupffer cells has already been achieved by modification of the sugar moieties of proteins or polymers. Coupling of galactose to, for instance, human serum albumin (HSA) leads to a specific accumulation of this neoglycoprotein in hepatocytes whereas addition of mannose to albumin causes uptake into Kupffer or endothelial cells. Increasing the net negative charge (for instance by succinylation of amine groups) results in uptake of the protein into endothelial cells via scavenger receptors. For a comprehensive review on carrier devices for cell specific delivery of drugs see D. K. F. Meijer and G. Molema, Sem. in Liver Dis. 15: 202-256, 1995. The benefits of such carrier devices for the development of novel pharmacotherapeutic interventions for various diseases has been well recognized. However, a specific carrier for drugs to HSC, the most important cell in the pathogenesis of liver fibrosis, has not been found yet.

SUMMARY OF THE INVENTION

The invention describes novel drug carriers which specifically accumulate in hepatic stellate cells (HSC). These carriers can be used for the targeting of all kinds of therapeutic agents, preferably anti-fibrotic drugs to HSC. The carriers may also be applied for the visualization of HSC for diagnostic purposes. The basis of the invention lies in the coupling of small cyclic proteins (oligopeptides), that contain specific receptor recognising peptides (RRPs) to soluble or particle type carriers (core carriers). The use of such a conjugate as a tool for targeting purposes has not been described. The target-receptors for these neo proteins, neo oligopeptides or oligopeptide carrier constructs are specific for HSC or are upregulated upon this cell type during the course of the disease. In the present study human serum albumin (HSA) is applied as the core-carrier, but the invention is not restricted to a specific protein or polymer. Each molecule with attachment sites for peptides is applicable as a carrier to HSC. The invention describes conjugates which bind to the platelet derived growth factor (PDGF)-receptor and conjugates which attach to the collagen type VI receptor. Both types of receptors are present in relatively high amounts upon HSC and are well characterized. The respective receptor-binding ligands are known.

Since these receptors are also upregulated in renal mesangial cells as well as fibroblasts in various organs during glomerulosclerosis, interstitial fibrosis, lung fibrosis or atherosclerosis, and since these pathological processes are accessible for macromolecules it is assumed that these carriers will also show a relative accumulation in these cell types during the course of these diseases. The conjugates described here may therefore also be applied as drug-carriers or carriers for diagnostic markers and/or for treatment of the above mentioned diseases.

The proliferation of HSC during the process of fibrosis is an important pathogenic factor. Cell-matrix interactions and the production of growth factors such as PDGF play a pivotal role in this proliferative response of HSC. Peptides which bind to the PDGF receptors or collagen type VI receptors will block the binding of endogenous PDGF or will interfere with cell-matrix interactions and therefore the oligopeptides described here may also exert an antiproliferative activity and consequently these oligopeptides may serve as anti-fibrotic or anti-sclerotic agents themselves.

Also other receptors may be targeted using this new approach. Transforming Growth Factor β (TGFβ), interleukin 1β (II 1β), and Tumor Necrosis Factor α (TNFα) are other important mediators during chronic inflammatory processes and the receptors for these cytokines are upregulated upon HSC as well as upon endothelial cells and Kupffer cells in the liver. The ligands for these receptors are well characterized and similar to the PDGF-receptor or collagen VI-receptor recognizing proteins, cyclic peptides recognizing the binding site for these receptors can be prepared and coupled to a core-protein such as albumin. A relative accumulation of these conjugates can be expected into the target cell expressing the particular receptors. Most of the cytokines contain a RGD sequence (arg-gly-asp). This is the (putative) cell attachment site and in combination with additional amino acids it will determine the specificity for the individual cytokines and growth hormone receptors. Coupling this RGD sequence and accompanying amino acids to a carriermolecule using the approach described here is feasible. The invention also includes the preparation of oligopeptides in which more than one receptor recognizing domain for the same receptor are combined and peptide constructs in which different receptor recognizing domains for different types of receptors are combined. The particular oligopeptide constructs containing a single or more than one receptor recognizing domain can be used as such, as intrinsic active substances but also for the preparation of drug conjugates (pro-drugs) and be employed to prepare larger drug carriers by coupling of the oligopeptides to either proteins, soluble and particulate polymeric carriers and lipoid carriers (liposomes, neolipoproteins, micelles) that subsequently can be used for covalent binding and/or inclusion or association of therapeutic agents for the purpose of cell-specific drug targetting. The application of such carriers is not limited to the treatment or diagnosis of fibrotic processes but also to other chronic and acute inflammatory processes such as, for instance, rheumatoid arthritis, Crohn's disease, colitis ulcerosa, glomerulonephritis and sepsis.

BRIEF DESCRIPTION OF THE DRAWINGS

FIG. 1-a shows organ distribution of human serum albumin (HSA) conjugated with 10 to 12 cyclic oligopeptides recognizing the PDGF-receptor in normal rats.

FIG. 1-b shows organ distribution of human serum albumin (HSA) conjugated with 10 to 12 cyclic oligopeptides recognizing the PDGF-receptor in rats with liver fibrosis induced by bile duct ligation (3 weeks after the operation).

FIG. 1-c represents the organ distribution of unmodified HSA.

FIG. 2-a shows organ distribution of human serum albumin (HSA) conjugated with 10 to 12 cyclic oligopeptides recognizing the collagen type VI-receptor in normal rats.

FIG. 2-b shows organ distribution of human serum albumin (HSA) conjugated with 10 to 12 cyclic oligopeptides recognizing the collagen type VI-receptor in rats with liver fibrosis induced by bile duct ligation (3 weeks after the operation).

FIG. 3-b shows, as seen from the arrowheads, the modified albumin co-localizes with the marker for HSC (desmin).

FIG. 4 is a graph representing in vitro displacement of radiolabeled PDGF-BB from its receptor upon 3T3-fibroblasts by HSA-PDGF receptor-binding peptide conjugates (pPB-HSA, closed blocks), HSA (open blocks) or uncoupled PDGF-receptor binding peptides (pPB, open circles).

FIG. 5 is a graph of the organ distribution of radiolabeled M6P$^x$-HSA in fibrotic rats (three weeks after bile duct ligation), 10 minutes after intravenous administration of the modified HSA.

FIG. 6 is a graph of the binding and uptake of radiolabeled M6P$_{28}$-HSA in human liver tissue at the reported temperatures.

DETAILED DESCRIPTION OF THE INVENTION

Figure 3A:
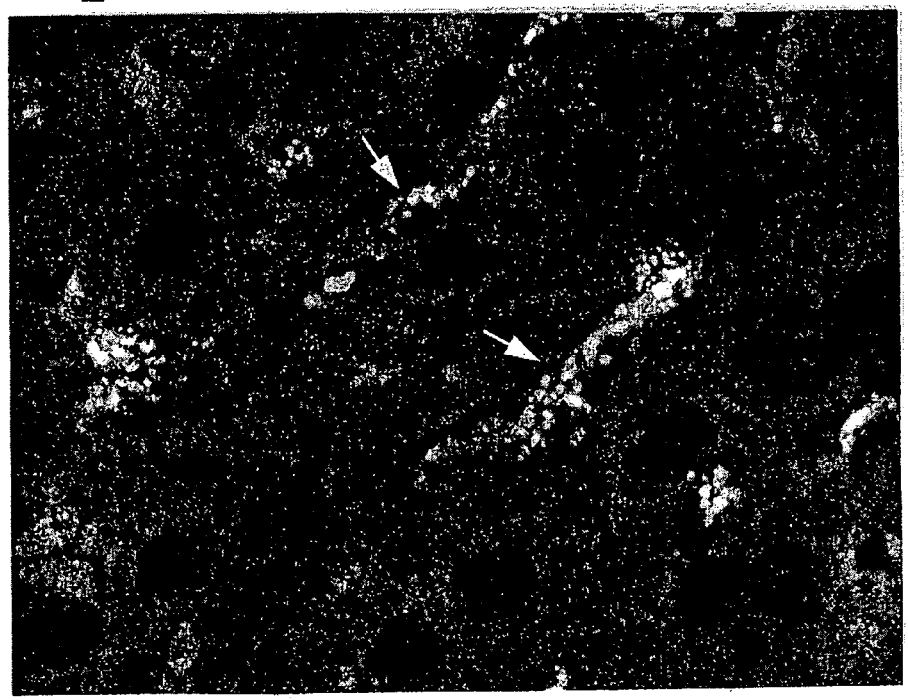
FIG. 3-a shows that after intravenous administration of modified protein, the albumin derivatives can be imuunhistochemically detected in a non-parenchymal cell type of the liver using a polyclonal antibody against albumin.
Figure 3B:
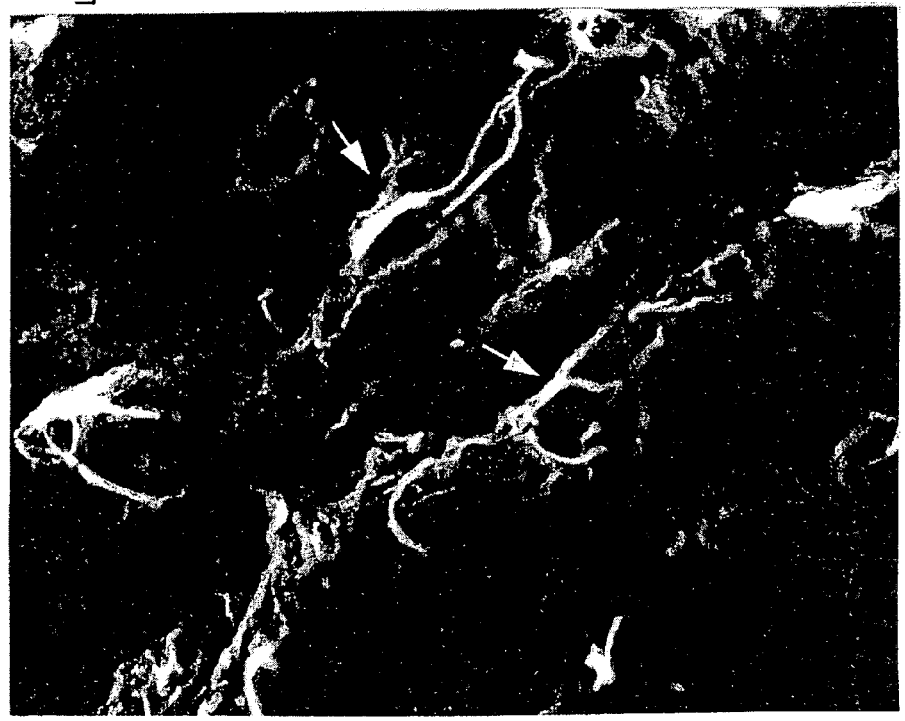

A compound according to the invention comprises a carrier molecule, said carrier molecule being linked to a further molecule, said further molecule being at least one cyclic peptide, said cyclic peptide comprising in the cyclic peptide portion thereof at least one sequence containing at least one specific receptor recognising peptide (RRP) and with the proviso the compound is not a naturally occurring receptor agonist or antagonist. Suitably in such a compound according to the invention the RRP is of a receptor specific for Hepatic Stellate Cells (HSC) or a receptor that is upregulated on HSC during disease.

The RRP can by way of example be the agonist or antagonist of a receptor selected from the group of receptors consisting of PDGF receptor, collagen type VI receptor, cytokine receptor such as TGFβ, TNFα and interleukin 1β.

Suitably, when the RRP is of a collagen type VI receptor, cytokine receptor such as TGFβ, TNFα and interleukin 1β, the cyclic portion of the cyclic peptide comprises at least the amino acid sequence RGD or KPT (1ys-pro-thr) in the cyclic portion thereof. By way of example the cyclic portion of the cyclic peptide comprises at least an amino acid sequence selected from X*YRGDYX* (Xaa(Xaa)$_n$-arg-gly-asp-(Xaa)$_n$-Xaa) and X*YKPTYX* (Xaa-(Xaa)$_n$-1ys-pro-thr-(Xaa)$_n$-Xaa) wherein X* represents the location of cyclisation and Y represents at least one amnio acid or a sequence of amino acids up to a length such that the receptor binding capacity of the cyclic peptide is retained. In an preferred embodiments, X* represents the location of attachment to the carrier molecule. In an embodiment illustrating the above, when the receptor agonist is of a collagen type VI receptor has a cyclic portion of the cyclic peptide comprising the amino acid sequence X*GRGDSPX* (Xaa-gly-arg-gly-asp-ser-pro-Xaa). Suitably, it will comprise the sequence-cysteine-glycine-arginine-glycine-aspartic aicd-serine-proline-cysteine. SEQ ID NO:1.

Suitably when the receptor agonist is of an interleukin 1 beta receptor, the cyclic peptide can comprise the amino acid sequence X*DKPTLX* (Xaa-asp-lys-pro-thr-lys-Xaa). SEQ ID NO:2.

Alternatively, when the receptor agonist is of PDGF receptor, the cyclic portion of the cyclid peptide can comprise the amino acid sequence X*SRNLIDCX* (Xaa-ser-arg-asn-leu-ile-asp-cys-Xaa), wherein X* represents the location of cyclisation. SEQ ID NO:3. In a preferred emodiment X* represents the location of attachment to the carrier molecule. Such a compound will bind to the PDGF receptor alha and beta subtypes. Suitably, it will comprise the sequence -cysteine-serine-arginine-asparagine-leucine-isoleucine-aspartic acid-cysteine.

In any of the embodiments according to the invention that are described X* can be a cysteine residue.

Only some crucial amino acids for the cyclic peptides are provided here. The oligopeptide may be elongated without causing a change in the cellular distribution pattern in vivo. Cyclisation of these peptides can be achieved for example by a disulfide bond between both cysteine groups. The free amine (a-amine) in one cysteine residue can be used to couple the oligopeptide to the carrier molecule. For example to the amine groups in a core-molecule like albumin, using succinimide-acetyl thioacetate (SATA). Coupling of more than one oligopeptide to albumin can be readily done. Attachment of the cyclic peptides to a carrier molecule via a biodegradable spacer, causing local release of the cyclic peptides, is also feasible. The examples provided here describe conjugates with multiple oligopeptides per HSA molecule, leaving enough free reactive groups within the core-protein (hydroxyl, amine or sulphate groups) to attach additional drugs or other chemicals. These conjugates selectively accumulate in HSC of normal and diseased livers.

The cyclic portion of the cyclic peptide can suitably comprise multiple RRP sequences. The cyclic portion of the cyclic peptide can comprise multiple RRP sequences directed at at least two different types of receptors. Obviously they can also be directed at the same type of receptor. Combinations of various receptor agonist sequences are naturally also possible. Thus a compound according to the invention in any of the embodiments defined may comprise multiple cyclic peptides directed at the same or different subtypes of receptors or may comprise multiple but similar oligopeptides that contain more than one identical or different RRP sequence directed at the same receptor or different receptors on the particular cell type respectively. By way of example a compound according to the invention, wherein the carrier molecule is linked to more than one cyclic peptide can suitably comprise 5-15 cyclic peptides as defined in any of the embodiments above.

A person skilled in the art will realise numerous types of carrier molecules can be applied. The carrier molecule can suitably be selected from endogenous plasma proteins e.g. albumin, lactoferrin, alkaline phosphatase, superoxide dismutase, alpha2 macroglobulin and fibronectin. They are to be pharmaceutically acceptable and of a size such that they preferably are not lost due to the renal excretion thereof. Such compounds are suitably larger than 5000 Daltons. Suitable examples of the carrier molecule can be selected from the group of carrier molecules consisting of proteins, oligo or polypeptides, immunoglobulins or parts thereof, oligonucleotides, disaccharides, polysaccharides, biodegradable synthetic polymers, liposomes, lipid particles, biocompatible polymers in the form of microspheres or nanoparticles. Quite suitably in a compound according to this aspect of the invention the carrier molecule is the endogenous plasma protein albumin. The immunoglobulins can be mono or polyclonal. Parts of immunoglobulins can comprise Fab' fragments or single chain Ig. Humanised antibodies and bispecific antibodies are envisaged. In the case of human administration carriers that occur naturally in humans are preferred. For the sake of easy linkage of the carrier molecule to the cyclic peptide the carrier molecule preferably comprises free reactive groups such as hydroxyl, amine or sulphate. The carrier molecule can suitably be linked to the cyclic peptide via a biodegradable spacer. The carrier molecule can itself be a drug, the activity of which is not impaired by linking the cyclic peptide to it.

In an alternative embodiment of the invention the carrier molecule in the compound can comprise additional drugs or chemicals linked thereto.

The invention also covers a pharmaceutical composition comprising a compound according to any of the aforementioned embodiments as targeting ingredient and any pharmaceutically acceptable carrier. A pharmaceutical composition according to the invention comprises a compound in any of the embodiments mentioned above as pharmaceutically active ingredient in combination with any pharmaceutically acceptable additional carrier. In an alternative embodiment the pharmaceutical composition can further comprise a drug biodegradably attached to the compound. It is also possible for the compound to further comprise a diagnostic marker attached thereto. A pharmaceutical composition according the invention will be in a pharmaceutical dosage form. Such a dosage form can comprise sprayable, injectable or infusable solutions or solids or dosage forms for pulmonary or other administration routes. Also a pharmaceutical composition according to the invention can be in a topical form. In the case of parenteral administration a systemically acceptable form should be composed. This means it can enter the bloodstream without causing clotting or inadmissibly toxic reactions.

The invention is also directed at application of a compound according to the invention in any of the abovementioned embodiments as active targeting ingredient for manufacturing a pharmaceutical composition according to the invention for therapy, prophylaxis or diagnosis of chronic diseases. Examples from this group consist of fibrotic disease, sclerotic disease and chronic or acute inflammatory processes such as glomerulosclerosis, interstitial fibrosis, atherosclerosis, rheumatoid arthritis, Crohns disease, colitis ulcerosa, glomerulonephritis, lung fibrosis and sepsis. Suitably use of a compound according to the invention as active targeting ingredient for manufacturing a pharmaceutical composition according to the invention for therapy, prophylaxis or diagnosis of a disease related to proliferation of HSC is also envisaged as forming a particularly useful application to be covered by the invention. A method of targeting HSC, said method comprising administration in a pharmaceutically acceptable amount and form of a compound or a pharmaceutical composition according to the invention to a subject or a tissue sample of a subject is covered by the invention. The person skilled in the art will adjust the dosage to be applied to the manner of application, size, weight, state of health etc of the subject to which administration is to occur. Administration can occur in any manner known per se for administration of medicament.

The invention also covers a method of therapy, diagnosis or prophylaxis of a disease related to HSC, said method comprising administration in a pharmaceutically acceptable amount and form of a compound or a pharmaceutical composition according to the invention to a subject or a tissue sample of a subject. Particularly such disease can be one selected from the group consisting of fibrotic disease, sclerotic disease and chronic or acute inflammatory processes such as glomerulosclerosis, interstitial fibrosis, lung fibrosis, atherosclerosis, rheumatoid arthritis, Crohns disease, colitis ulcerosa, glomerulonephritis and sepsis. The method comprises administration in a pharmaceutically acceptable amount and form of the compound or pharmaceutical composition according to the invention to a subject or a tissue sample of a subject. The person skilled in the art will adjust the dosage to be applied to the manner of application, size, weight, state of health etc of the subject to which administration is to occur. Administration can occur in any manner known per se for administration of therapeutic agents.

This further aspect of the invention will be illustrated but not limited in the following examples.

EXAMPLE 1

Normal rats and rats with liver fibrosis (3 weeks after bile duct ligation) received an intravenous injection of 10 mg/kg b.w. PDGF receptor-binding peptides conjugated with HSA. Based upon the results of the organ distribution studies with radiolabeled conjugates (FIG. 1), rats were sacrificed after ten minutes and samples of the liver and bone (from ribs, front paw, rear paw and the back) were removed for histochemical examination. No accumulation of this HSA-peptide conjugate was detectable in bone samples, whereas abundant staining was found in tissue samples. Upon cryostat sections of these livers double stainings were performed with anti-HSA antibodies and antibodies against Kupffer cells (ED1), endothelial cells (RECA-1), myofibroblasts (anti-actin antibodies) or hepatic stellate cells (desmin and GFAP antibodies). Subsequently, the number of double positive cells (HSA+ and cell marker+) were counted and related to the total number of HSA positive cells in the same area. Results of the quantitative evaluation of the carrier uptake in the liver are summarized in table 1.

TABLE 1

Relative accumulation of HSA modified with collagen VI-receptor recognising peptides (pCVI-HSA) or PDGF receptor-recognising peptides (pPB-HSA) in non-parenchymal cells of the liver. The number of HSA-positive cells was related to the number of cells double-positive for HSA and a HSC marker (desmine), or a EC marker (HIS 52), or a KC marker (ED2) or a PC marker (glycogen).

|  | % HSC | % EC | % KC | PC |
| --- | --- | --- | --- | --- |
| pCVI-HSA | 73 ± 14 | 30 ± 10 | 16 ± 11 | – |
| pPB-HSA | 72 ± 18 | 16 ± 6 | 11 ± 6 | + |

HSC = hepatic stellate cells,
EC = endothelial cells,
KC = Kupffer cells,
PC = parenchymal cells

EXAMPLE 2

Normal rats and rats with liver fibrosis (3 weeks after bile duct ligation) received an intravenous injection of 10 mg/kg b.w. collagen VI receptor-binding peptides conjugated with HSA. Based upon the results of the organ distribution studies with radiolabeled conjugates (FIG. 2), rats were sacrificed after ten minutes and samples of the liver and bone (from ribs, front paw, rear paw and the back) were removed for histochemical examination. No accumulation of this HSA-peptide conjugate was detectable in bone samples, whereas abundant staining was found in tissue samples. Upon cryostat sections of these livers double stainings were performed with anti-HSA antibodies and antibodies against Kupffer cells (ED1), endothelial cells (RECA-1), myofibroblasts (anti-actin antibodies) or hepatic stellate cells (desmin and GFAP antibodies). Subsequently, the number of double positive cells (HSA+ and cell marker+) were counted and related to the total number of HSA positive cells in the same area. Results of the quantitative evaluation of the carrier uptake in the liver are summarized in table 1.

EXAMPLE 3

Another cyclic oligopeptide recognizing the PDGF-receptor can be described as follows:
-cysteine-arginine-lysine-lysine-proline-cysteine- (C*RKKPC*), where the cysteines (C*) represent the cyclisizing residues.

Only some crucial amino acids for the PDGF-binding peptide are provided here. The oligopeptide may be elongated without causing a change in the cellular distribution pattern in vivo. Cyclisation of this peptide can be achieved by a disulfide bond between both cysteine groups, whereas the free amine in one cysteine residue can be used to couple the oligopeptide to a core-molecule like albumin. Coupling of more than one oligopeptide to albumin can be readily done.

EXAMPLE 4

A cyclic peptide which binds to the interleukin 1'-receptor can be described as follows:

-cysteine-aspartic acid-lysine-proline-threonine-leucine-cysteine-(C*DKPTLC*)

where the cysteines (C*) represent the cyclisizing residues.

The receptor binding properties of the tripeptide lysine-proline-threonine (KPT) has been reported (Ferreira et al., Nature 334: 698, 1988). Two or more additional amino acids, preferably the two adjacent amino acids in the native interleukin 1β molecule on both sites of this tripeptide, are in this example attached to this tripeptide. Subsequently, the terminal cysteine residues allow for cyclysation of this oligopeptide and coupling of this peptide to a macromolecule. In this way, the interleukin 1β binding site is exposed to its receptor similar to the PGDF— and collagen VI receptor binding peptides. This conjugate may also serve as a carrier for therapeutic or diagnostic agents for the treatment of inflammatory processes.

DESCRIPTION OF THE DRAWINGS

FIG. 1: Organ distribution of human serum albumin (HSA) conjugated with 10 to 12 cyclic oligopeptides recognizing the PDGF-receptor in normal rats [figure A] and in rats with liver fibrosis induced by bile duct ligation (3 weeks after the operation) [fig.B]. Figure C represents the organ distribution of unmodified HSA. Organs were removed 10 minutes after intravenous administration of radiolabeled ($^{125}I$) protein and analyzed using a gamma-counter. The results are expressed as the mean±SD (n=3 per group). Note the accumulation of modified HSA in livers of normal and diseased rats, whereas native HSA remains in the blood.

FIG. 2: Organ distribution of human serum albumin (HSA) conjugated with 10 to 12 cyclic oligopeptides recognizing the collagen type VI-receptor in normal rats [figure A] and in rats with liver fibrosis induced by bile duct ligation (3 weeks after the operation) [fig. B]. Organs were removed 10 minutes after intravenous administration of radiolabeled ($^{125}I$) protein and analyzed using a gamma-counter. The results are expressed as the mean±SD (n=3 per group). Note the accumulation of modified HSA in livers of normal and diseased rats.

FIG. 3: Intrahepatic distribution of HSA modified with 10-12 collagen type VI-receptor binding peptides in fibrotic rats (3 weeks after bile duct ligation). 10 minutes after intravenous administration of modified protein, the albumin derivatives can be imuunhistochemically detected in a non-parenchymal cell type of the liver using a polyclonal antibody against albumin [fig. A]. The modified albumin co-localizes with the marker for HSC (desmin) [see arrowheads, fig. B].

FIG. 4: In vitro displacement of radiolabeled PDGF-BB from its receptor upon 3T3-fibroblasts by HSA-PDGF receptor-binding peptide conjugates (pPB-HSA, closed blocks), HSA (open blocks) or uncoupled PDGF-receptor binding peptides (pPB, open circles). Note the strong inhibition of binding of native PDGF to fibroblasts induced by the modified HSA, but not by native HSA or the oligopeptides alone.

FIG. 5. The organ distribution of radiolabeled M6P$^x$-HSA in fibrotic rats (three weeks after bile duct ligation), 10 minutes after intravenous administration of the modified HSA. x=2, 4,10, 21, and 28. Note that proteins substituted with 2,4 or 10 M6P molecules per HSA remain in the blood, whereas proteins with high amounts of substitution accumulate in the liver.

FIG. 6. Binding and uptake of radiolabeled M6P$_{28}$-HSA in human liver tissue at 4 degrees Celcius respectively 37 degrees Celsius. $^{125}$I-labeled modified albumin was incubated with slices (10 mg) obtained from patients with a normal liver function. (TX=transplantation liver) or from patients with liver Cirrhosis (Cir). Note the high accumulation of neo-glycoprotein in human liver slices as compared to native HSA.

BACKGROUND INFORMATION TO A FURTHER ASPECT OF THE INVENTION

An increased expression of the Insulin Growth Factor II/mannose-6-phosphate (IGFII/M6P) receptor has been reported upon hepatic stellate cells in particular after activation of this cell type. This led to the idea of coupling mannose-6-phosphate (M6P) to a core-protein and the use of such a neo-glycoprotein as a drug carrier to HSC. The degree of substitution of M6P to HSA necessary for this purpose could not be deduced from the present state of the art. We have found that a quite high degree of substitution is required for efficient targeting. Introduction of only a few groups was not particularly successful. The invention thus provides a novel type of drug carrier to the hepatic stellate cells (HSC). The carrier can be used for the targeting of all kinds of therapeutic agents, preferably anti-fibrotic agents to HSC, or may be applied for the visualization of HSC for diagnostic purposes.

As it was also reported that this receptor played a role in the activation of latent TGF-beta and TGF-beta is known to be a pro-fibrogenic growth factor which is a very important mediator during fibrosis the compound according to this further aspect of the invention should also be useful for diagnosis, prophylaxis and therapy of fibrotic diseases. Mannose-6-phosphate substituted proteins may also interfere with the activation of latent TGF-beta and this carrier may therefore have an antifibrotic action of its own.

DETAILED DESCRIPTION OF THE FURTHER ASPECT OF THE INVENTION

The invention in a further aspect is directed at a compound capable of recognising and binding a mannose 6 phosphate receptor said compound comprising a carrier molecule linked to a molecule capable of recognising and capable of binding mannose-6-phosphate receptor, said molecules recognising and capable of binding mannose-6-phosphate receptor being present on the carrier molecule in at least an amount sufficient to occupy at least 20% of the carrier molecule linking sites for said molecules recognising and capable of binding mannose-6-phosphate receptor, with the proviso the compound is not latent tumor growth factor beta, thyroglobulin or a lysosomal protein. The latter are known proteins that are also known to comprise terminal mannose 6 phosphate groups and as such will bind to the mannose 6 phosphate receptor. They are excluded as compounds according to the invention. The substitution degree can be higher than 30% even as high as 40 or 50%. A suitable example of the molecule capable of recognising and capable of binding mannose-6-phosphate receptor is mannose 6 phosphate.

In a compound according to this aspect of the invention the carrier molecule can be selected from the group consisting of proteins, oligo or polypeptides, immunoglobulins or parts thereof, oligonucleotides, disaccharides, polysaccharides, biodegradable synthetic polymers, liposomes, lipid particles, biocompatible polymers in the form of microspheres or nanoparticles. The carrier molecule can suitably be selected from endogenous plasma proteins e.g. albumin, lactoferrin, alkaline phosphatase, superoxide dismutase, alpha2 macroglobulin and fibronectin. The immunoglobulins can be mono or polyclonal. Parts of immunoglobulins can comprise Fab' fragments or single chain Ig. Humanised antibodies and bispecific antibodies are envisaged. Quite suitably in a compound according to this aspect of the invention the carrier molecule is the endogenous plasma protein albumin. A person skilled in the art will realise numerous types of carrier molecules can be applied. They are to be pharmaceutically acceptable and of a size such that they preferably are not lost due to the renal excretion thereof. Such compounds are suitably larger than 50000 Daltons.

Quite specifically in a preferred embodiment of a compound according to this aspect of the invention at least 10 molecules capable of recognising and capable of binding mannose-6-phosphate receptor are linked to the carrier molecule. The carrier based upon macromolecules substituted with mannose-6-phosphate residues with substitution of more than 10 mannose-6-phosphate residues per macromolecule has been found exceptionally appropriate for proper targeting. The carrier molecule was human serum albumin.

The invention also covers a pharmaceutical composition comprising a compound according to any of the aforementioned embodiments of the further aspect of the invention disclosed as targeting ingredient and any pharmaceutically acceptable carrier. A pharmaceutical composition according to the invention comprises a compound in any of the embodiments mentioned above as pharmaceutically active ingredient in combination with any pharmaceutically acceptable additional carrier. In an alternative embodiment the pharmaceutical composition can further comprise a drug biodegradably attached to the compound. It is also possible for the compound to further comprise a diagnostic marker attached thereto. A pharmaceutical composition according the invention will be in a medicinal dosage form. Such a dosage form can comprise sprayable, injectable or infusable solutions or solids or dosage forms for pulmonary or other administration routes. Also a pharmaceutical composition according to the invention can be in a topical form but will preferably be in a systemically acceptable form. This means it can enter the bloodstream without causing clotting or inadmissibly toxic reaction.

The invention is also directed at application of a compound according to the invention in any of the abovementioned embodiments as active targeting ingredient for manufacturing a pharmaceutical composition according to the further aspect of the invention just mentioned for therapy, prophylaxis or diagnosis of a disease selected from the group of chronic diseases, for example fibrotic disease, sclerotic disease and chronic or acute inflammatory processes such as glomerulosclerosis, interstitial fibrosis, lung fibrosis, atherosclerosis, rheumatoid arthritis, Crohns disease, colitis ulcerosa, glomerulonephritis and sepsis.

The invention is also directed at application of a compound according to the invention in any of the abovementioned embodiments as active targeting ingredient for manufacturing a pharmaceutical composition according to the further aspect of the invention just mentioned for therapy, prophylaxis or diagnosis of any of the following pathological conditions; cell proliferation associated pathology e.g. tumors, a disease related to proliferation of HSC, fibroblast proliferation associated pathology, endothelial cell proliferation associated pathology and osteoblast proliferation associated pathology.

The invention also covers a method of targeting proliferating cells, preferably tumor cells, HSC, fibroblasts, endothelial cells and osteoblasts said method comprising administration in a pharmaceutically acceptable amount and form of a compound or a pharmaceutical composition according to the aspect of the invention just described to a subject or a tissue sample of a subject.

In an alternative embodiment it also covers a method of targeting proliferating cells, preferably tumor cells, HSC, fibroblasts, endothelial cells and osteoblasts said method comprising administration in a pharmaceutically acceptable amount and form of a compound or a pharmaceutical composition according to the further aspect of the invention just described to a subject or a tissue sample of a subject. Alternatively it covers a method of therapy, diagnosis or prophylaxis of a disease related to proliferating cells, preferably tumor cells, HSC, fibroblasts, endothelial cells and osteoblasts, said method comprising administration in a pharmaceutically acceptable amount and form of a compound or a pharmaceutical composition according to the further aspect of the invention to a subject or a tissue sample of a subject. Specifically it covers a method of therapy, diagnosis or prophylaxis of a disease related to HSC, said method comprising administration in a pharmaceutically acceptable amount and form of a compound or a pharmaceutical composition as described for the further aspect of the invention to a subject or a tissue sample of a subject. A method of therapy, prophylaxis or diagnosis of a disease selected from the group consisting of fibrotic disease, sclerotic disease and chronic or acute inflammatory processes such as glomerulosclerosis, interstitial fibrosis, lung fibrosis, atherosclerosis, rheumatoid arthritis, Crohns disease, colitis ulcerosa, glomerulonephritis and sepsis, said method comprising administration in a pharmaceutically acceptable amount and form of a compound or a pharmaceutical composition as described for the further aspect of the invention to a subject or a tissue sample of a subject also falls within the scope of the invention.

This further aspect of the invention will be illustrated but not limited in the following examples.

EXAMPLE 5

Mannose 6-phosphate was covalently coupled to human serum albumin (HSA) in two steps. First, p-nitrophenyl-α-D-mannopyranoside (Sigma, St. Louis, USA) was phosphorylated according to standard procedures. The molecular weight (MW 381) and purity of the obtained crystalline product p-nitrophenyl-6-phospho-α-D-mannopyranoside was verified by mass spectrometry. Subsequently, the nitro-group was reduced with 10% palladium on active carbon (Aldrich Chemie GmbH, Steinheim, Germany) under hydrogen atmosphere of 1 atm. The obtained product p-aminophenyl-6-phospho-α-D-mannopyranoside was coupled to HSA by activation with thiophosgene. By variations in the molar ratio HSA: p-nitrophenyl-6-phospho-α-D-mannopyranoside, a series of neoglycoproteins ($M6P_x$-HSA) were obtained, x=2, 4, 10, 21, or 28. The $M6P_x$-HSA preparations were further purified and characterized according to standard procedures.

A tracer dose of modified HSA ($^{125}$I labelled) was intravenously administered to normal and fibrotic rats (three weeks after bile duct ligation). Ten minutes after injection of these compounds, rats were sacrificed and all organs were removed. As can also be seen in FIG. 5, the degree of substitution of mannose 6-phosphate to HSA strongly influenced liver uptake. HSA with a low degree of sugar loading (x=2-10) accumulated for 2±1% to 9±0.5% in fibrotic rat livers, while the rest of the dose remained in the circulation. An increase in the molar ratio of M6P:HSA up to 28 caused a gradual increase in liver accumulation (to 59±9% of the dose).

In addition, the intrahepatic distribution of modified HSA was examined immunohistochemically. Modified HSA was administered to rats (10 mg/kg b.w.) and 10 minutes after the injection samples from the liver, spleen, kidney, and bone were histochemically examined. We observed that the more mannose 6-phosphate was linked to HSA, the higher the uptake was in HSC. Quantitative evaluation of liver sections ten minutes after administration of modified HSA revealed that M6P10-HSA accumulated for 19±10% in HSC. In contrast, 69±12% of the intrahepatic staining for M6P28-HSA was found in HSC, whereas 20±6% was found in Kupffer cells and 17±6% in endothelial cells. No uptake was detected in hepatocytes and bile duct epithelial cells. Also no staining for modified HSA was found in other organs.

EXAMPLE 6

$M6P_{21}$-bovine serum albumin (BSA) and $M6P_{28}$-HSA, synthesized and characterized according to standard procedures, were radiolabeled with $^{125}$I. The intrahepatic uptake of these neo-glycoproteins was measured in human liver slices. These slices (+10 mg liver tissue with a thickness of approximately 10 cells) were obtained from patients with normal liver function and from cirrhotic patients. Significant intrahepatic accumulation of radiolabeled BSA and HSA derivates was found within one hour after co-incubation with these slices, whereas unmodified BSA or HSA was not taken up by the human tissue samples (see FIG. 6).

EXAMPLE 7

Pyrrolidine-dithiocarbamate (PDTC, which is an inhibitor of the transcription factor NF-kappaB) was attached to $M6P_{28}$-HSA by coupling the carboxylic groups of PDTC to lysine groups of HSA according to standard procedures. This compound was administered to rats with liverfibrosis induced by bile duct ligation. Rats receiving this conjugate 1, 3 and 5 days after the bile duct ligation displayed less proliferation of HSC in the parenchymal area at day 7 as compared to rats receiving no treatment or PDTC alone after induction of fibrosis. HSC were demonstrated in cryostat sections with anti-desmine and anti-Glial Fibrillar Acidic Protein (GFAP) antibodies and standard indirect immunoperoxidase techniques.

The invention claimed is:

1. A method for targeting cells for diagnostic or drug-delivery involved in sclerotic and/or fibrotic diseases, and in which cells the Insulin Growth Factor II/mannose-G-phosphate receptor (IGFII/M6P receptor) is upregulated during disease, in a subject in need thereof or in a tissue sample of a subject, using, in a pharmaceutically acceptable amount and form a carrier molecule that comprises human serum albumin (HSA) or bovine serum albumin (BSA), wherein said carrier molecule is linked to at least one further molecule, said further molecule being mannose-6-phosphate, wherein at least 10 to 28 molecules of mannose-6-phosphate are linked to said carrier.

2. A method according to claim 1, wherein the cells are Hepatic Stellate Cells (HSC).

3. A method according to claim 1, wherein the carrier molecule comprises additional drugs or chemicals linked thereto.

4. A method according to claim 1, wherein the cells involved in a sclerotic and/or a fibrotic disease are cells involved in a disease selected from the group consisting of liver fibrosis, kidney fibrosis, lung fibrosis, atherosclerosis and chronic or acute inflammatory processes, Crohn's disease, colitis ulcerosa, glomerulonephritis, sepsis and tumor-cell proliferation associated pathology, fibroblast proliferation associated pathology, endothelial cell proliferation associated pathology and osteoblast proliferation associated pathology.

5. The method according to claim 1, wherein said carrier comprises human serum albumin (HSA).

6. The method according to claim 1, wherein said carrier comprises bovine serum albumin (BSA).

* * * * *

SEQUENCE LISTING

<160> NUMBER OF SEQ ID NOS: 5

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Variable amino acid; location of cyclisation
<220> FEATURE:
<221> NAME/KEY: MOD_RES
<222> LOCATION: (8)
<223> OTHER INFORMATION: Variable amino acid; location of cyclisation

<400> SEQUENCE: 1

Xaa Gly Arg Gly Asp Ser Pro Xaa
 1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Variable amino acid; location of cyclisation
<220> FEATURE:
<221> NAME/KEY: MOD_RES
<222> LOCATION: (7)
<223> OTHER INFORMATION: Variable amino acid; location of cyclisation

<400> SEQUENCE: 2

Xaa Asp Lys Pro Thr Leu Xaa
 1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Variable amino acid; location of cyclisation
<220> FEATURE:
<221> NAME/KEY: MOD_RES
<222> LOCATION: (9)
<223> OTHER INFORMATION: Variable amino acid; location of cyclisation

<400> SEQUENCE: 3

Xaa Ser Arg Asn Leu Ile Asp Cys Xaa
 1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 4

Cys Arg Lys Lys Pro Cys
  1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Cys Asp Lys Pro Thr Leu Cys
  1               5
```